(12) United States Patent
Roy

(10) Patent No.: US 11,337,854 B2
(45) Date of Patent: May 24, 2022

(54) INTRAOCULAR IRIS PROTECTOR AND METHOD OF USING SAME

(71) Applicant: Francis Roy, Trois-Rivières (CA)

(72) Inventor: Francis Roy, Trois-Rivières (CA)

(*) Notice: Subject to any disclaimer, the term of this patent is extended or adjusted under 35 U.S.C. 154(b) by 0 days.

(21) Appl. No.: 16/971,674

(22) PCT Filed: Feb. 21, 2019

(86) PCT No.: PCT/CA2019/050213
§ 371 (c)(1),
(2) Date: Aug. 20, 2020

(87) PCT Pub. No.: WO2019/161499
PCT Pub. Date: Aug. 29, 2019

(65) Prior Publication Data
US 2020/0405536 A1      Dec. 31, 2020

Related U.S. Application Data

(60) Provisional application No. 62/633,254, filed on Feb. 21, 2018.

(51) Int. Cl.
*A61F 9/007*          (2006.01)
(52) U.S. Cl.
CPC .................... *A61F 9/007* (2013.01)
(58) Field of Classification Search
CPC .................. A61F 9/007; A61F 9/0017; A61F 2009/00876; A61B 17/0231; A61B 17/0293; A61B 17/0206
See application file for complete search history.

(56) References Cited

U.S. PATENT DOCUMENTS 4,446,582 A  *  5/1984  Hanna ..................... A61F 2/148
                                                                     623/6.51
4,617,023 A  *  10/1986  Peyman .................... A61F 2/16
                                                                     623/6.45
(Continued)

FOREIGN PATENT DOCUMENTS

CN          203 763 350 U       8/2014
KR          10-1633346 B1       6/2016
RU           2 254 110 C1       6/2005

OTHER PUBLICATIONS

International Search Report and Written Opinion dated May 24, 2019 in connection with International Application No. PCT/CA2019/050213, 10 pages.

(Continued)

*Primary Examiner* — Kelly J Bekker
*Assistant Examiner* — Andrew P. Restaino
(74) *Attorney, Agent, or Firm* — Wolf, Greenfield & Sacks, P.C.

(57) ABSTRACT

An iris protector to reduce a likelihood of iris prolapse in an eye comprising an iris during an ophthalmic surgical procedure. The iris protector comprises an iris engaging portion and a plurality of engaging elements configured to facilitate the insertion and the removal of the iris protector inside the eye through an incision. Once inside the eye, the iris protector mechanically prevents a portion of the iris in the vicinity of the incision from prolapsing through the incision. The iris protector may be provided as part of a sterilized kit alone or with an applicator (e.g. tweezers, etc.), a manipulator or any combination thereof.

16 Claims, 11 Drawing Sheets

(56) References Cited

U.S. PATENT DOCUMENTS

| | | | |
|---|---|---|---|
| 6,228,093 B1 | 5/2001 | Tomalla | |
| 9,089,397 B2 | 7/2015 | Clarke | |
| 2012/0136322 A1* | 5/2012 | Alster | A61F 9/0026 |
| | | | 604/290 |
| 2014/0090653 A1* | 4/2014 | Clarke | A61F 9/04 |
| | | | 128/858 |

OTHER PUBLICATIONS

International Preliminary Report on Patentability dated Sep. 3, 2020 in connection with International Application No. PCT/CA2019/050213, 8 pages.

* cited by examiner

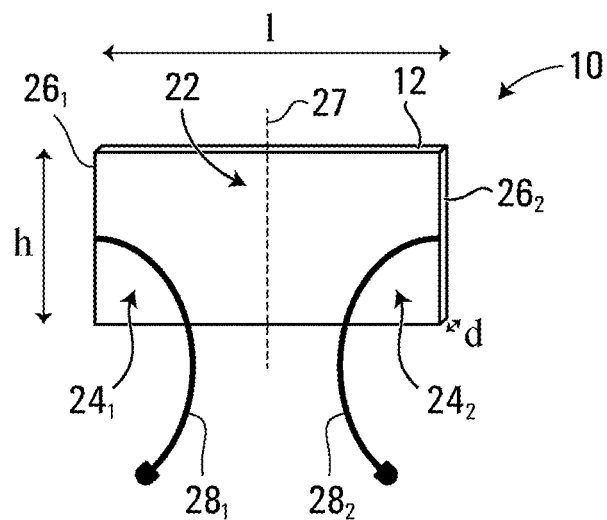
FIG. 1
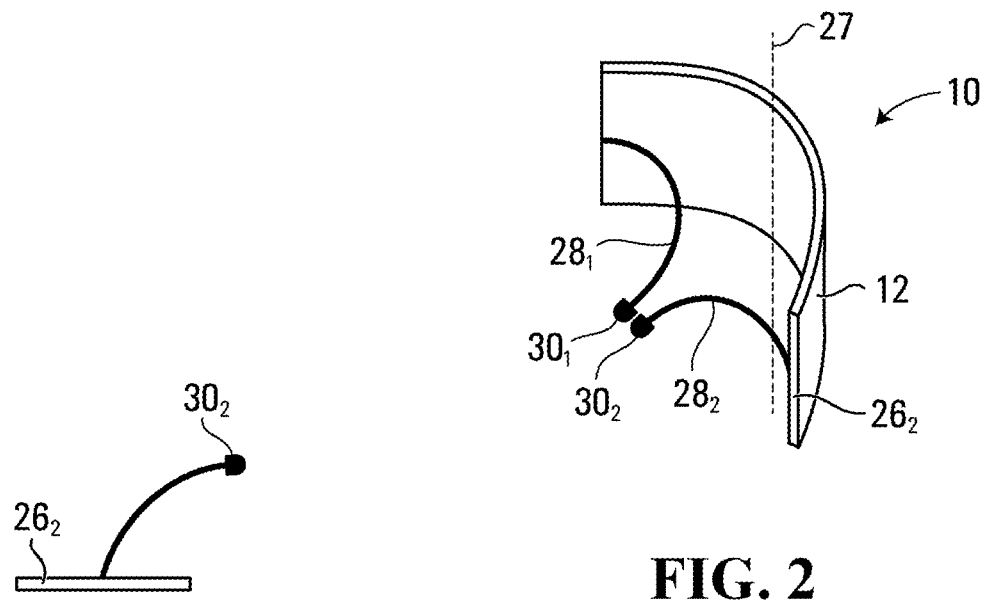
FIG. 3
FIG. 2

INTRAOCULAR IRIS PROTECTOR AND METHOD OF USING SAME

CROSS-REFERENCE TO RELATED APPLICATION

The present application is a 35 U.S.C. § 371 National Phase filing of International Application No. PCT/CA2019/050213, filed on Feb. 21, 2019, entitled "INTRAOCULAR IRIS PROTECTOR AND METHOD OF USING SAME," which claims priority to and the benefit of U.S. provisional patent application Ser. No. 62/633,254 filed on Feb. 21, 2018 by Francis Roy. The contents of the above-referenced applications are incorporated herein by reference in their entirety.

TECHNICAL FIELD

This disclosure relates to apparatuses, uses thereof and methods for reducing occurrences of prolapse of iris tissue through a surgical incision during an ophthalmic surgical procedure.

BACKGROUND

The iris is a thin, colored diaphragm that is situated anterior to the lens of the eye. Although the root of the iris is attached to the ciliary body, the rest of the iris is essentially unsupported. During ophthalmic surgical procedures such as cataract surgery, a small incision is typically made in the cornea either via laser or scalpel. A pressure inside the cornea that is less than a pressure in a region anterior to the iris (i.e., between the iris and the cornea) may cause the unsupported portion of the iris to prolapse through the incision. This is particularly prevalent in patients exhibiting intraoperative floppy iris syndrome (IFIS). Unless iris prolapse is addressed and treated immediately during the surgery, the result may be irremediable damage to the iris.

Known treatments of iris prolapse include the introduction of a dispersive visco-elastic material in the region of the prolapse to mechanically reposition the iris and the use of a spatula or other suitable blunt surgical instrument to mechanically reposition the iris during surgery. The latter however is prone to cause irremediable damage to the iris and thus its use is often avoided.

Several tools are currently available to maintain an appropriate dilatation of the iris in patients suffering from IFIS, such as iris hooks, Malyugin rings and pupil expanders. These generally mechanically maintain an appropriate dilation of the iris by engaging unsupported portions of the iris. However, none of these tools provide an efficient protection against iris prolapse since prolapse may occur via any iris portion, not only unsupported portions.

There is accordingly a need for improved surgical tools that may help alleviate the risk of iris prolapse during ophthalmic surgical procedures, notably in at-risk patients.

SUMMARY

This Summary is provided to introduce a selection of concepts in a simplified form that are further described below in the Detailed Description. This Summary is not intended to identify key aspects or essential aspects of the claimed subject matter.

According to one aspect of the disclosure there is provided an iris protector for use in reducing occurrences of prolapse of iris tissue during ophthalmic surgical procedures. The iris protector comprises a substantially planar iris engaging portion configured to rest directly on an iris once inserted inside an eye and folding handling members extending from the substantially planar iris engaging portion.

According to another aspect of the disclosure there is provided an iris protector for use in reducing occurrences of prolapse of iris tissue during ophthalmic surgical procedures. The iris protector comprises a substantially planar iris engaging portion configured to rest directly on an iris once inserted inside an eye and folding handling members extending from the substantially planar iris engaging portion. In use during a specific ophthalmic surgical procedure, the substantially planar iris engaging portion is inserted into a specific eye through an incision made in a peripheral region of a cornea of the specific eye and is positioned to rest on the iris of the specific eye and across the incision to mechanically prevent the iris from prolapsing through the incision. When the substantially planar iris engaging portion rests on the iris at least a portion of the folding handling members extend outside the eye through the incision.

According to another aspect of the disclosure there is provided a kit comprising the iris protector and a corresponding applicator.

According to yet another aspect of the disclosure there is provided a kit comprising the iris protector and a corresponding scalpel.

According to yet another aspect of the disclosure there is provided a kit comprising the iris protector and a corresponding manipulator.

According to yet another aspect of the disclosure there is provided a use of the iris protector to reduce a likelihood of iris prolapse in an eye comprising an iris during an ophthalmic surgical procedure.

According to yet another aspect of the disclosure there is provided an iris protector for use in reducing a likelihood of prolapse of iris tissue during an ophthalmic surgical procedure. The iris protector is configured for being inserted inside an eye through an incision, mechanically preventing the iris from prolapsing through the incision during the surgery and being removed from the eye through the incision by manipulating a portion of the iris protector located outside of the eye.

According to yet another aspect of the disclosure there is provided a method of reducing a likelihood of iris prolapse in an eye comprising an iris during an ophthalmic surgical procedure. The method comprises making an incision in a peripheral region of a cornea of the eye, inserting an iris protector inside the eye through the incision before a beginning of the ophthalmic surgical procedure, the iris protector mechanically preventing the iris from prolapsing through the incision during the ophthalmic surgical procedure, and removing the iris protector from the eye after an end of the ophthalmic surgical procedure by only manipulating a portion of the iris protector located outside of the eye.

According to yet another aspect of the disclosure there is provided an iris protector for use inside an eye comprising an iris during a surgery. The iris protector is configured for being inserted inside the eye through a surgical incision, mechanically preventing the iris from prolapsing through the incision during the surgery and projecting outside of the eye through the incision during the surgery.

According to yet another aspect of the disclosure there is provided an iris protector for use inside an eye comprising an iris during a surgery. The iris protector is configured for being inserted inside the eye in a folded configuration through a surgical incision, being positioned inside the eye only by allowing a transition from the folded configuration to an elongated configuration and mechanically preventing the iris from prolapsing through the incision during the surgery.

All features of exemplary embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments of the invention in conjunction with the accompanying drawings.

BRIEF DESCRIPTION OF THE DRAWINGS

A detailed description of embodiments is provided below, by way of example only, with reference to accompanying drawings, in which:

FIG. 1 shows an isometric view of a foldable iris protector having a cuboid iris engaging portion in an elongated configuration in accordance with a first specific embodiment;

FIG. 2 shows an isometric view of the iris protector of FIG. 1 in a partially folded configuration;

FIG. 3 shows a side-elevation view of the iris protector on FIG. 1;

Figure 4:
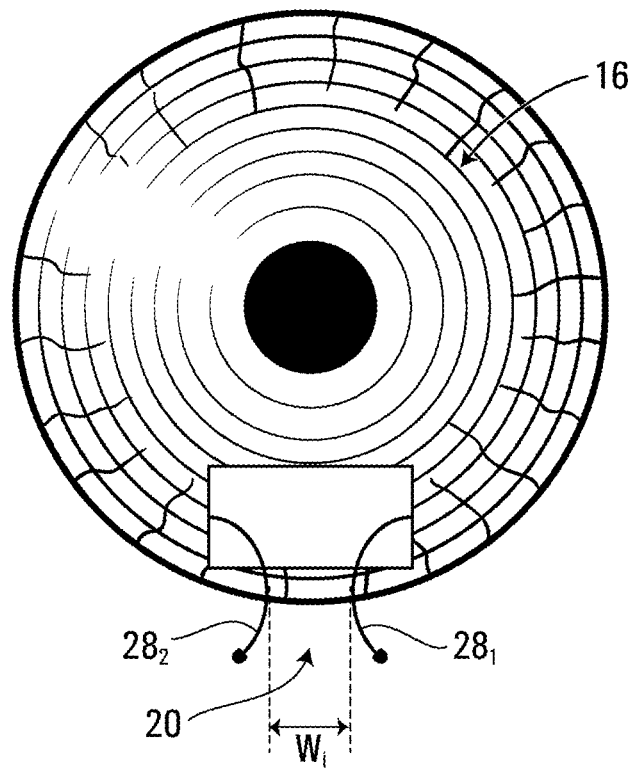
FIG. 4 shows a top plan view of the iris protector of FIG. 1 when inserted inside an eye.

In the drawings, embodiments of the invention are illustrated by way of examples. It is to be expressly understood that the description and drawings are only for the purpose of illustration and are an aid for understanding. They are not intended to be a definition of the limits of the invention.

DETAILED DESCRIPTION OF SOME EMBODIMENTS

A detailed description of one or more embodiments of the invention is provided below along with accompanying Figures that illustrate the principles of the invention. The invention is described in connection with such embodiments, but the invention is not limited to any embodiment. The scope of the invention is limited only by the claims. Numerous specific details are set forth in the following description in order to provide a thorough understanding of the invention. These details are provided for the purpose of non-limiting examples and the invention may be practiced according to the claims without some or all of these specific details. For the purpose of clarity, technical material that is known in the technical fields related to the invention has not been described in detail so that the invention is not unnecessarily obscured.

FIG. 1 shows an iris protector 10 in accordance with a first specific embodiment. In this embodiment, the iris protector 10 is foldable, that is the iris protector 10 can adopt an "elongated" configuration and a "folded" configuration.

According to this first embodiment, and with further reference to FIGS. 2-5, the iris protector 10 comprises a substantially planar iris engaging portion 12 generally configured to rest directly on an iris 16 once inserted inside an eye 14. The iris engaging portion 12 may be made of a resilient, shape-memory material such that the iris engaging portion 12 returns to the elongated configuration after being mechanically forced by a user into a folded configuration, as will be further described below. The material of the iris engaging portion 12 is biocompatible and the iris engaging portion 12 is generally configured not to cause damage to the iris 16 once resting on the iris 16. In some practical implementations, the iris engaging portion 12 may be made of material including polypropylene, a flexible surgical-grade polymer, silicon, acrylic, nitinol (nickel titanium) or any other suitable biocompatible material.

The iris engaging portion 12 may have any suitable shapes and dimensions. However, it is appreciated that the shape and dimensions of the iris engaging portion 12 should be selected to ensure that the iris protector 10 may be inserted inside the eye 14 in the folded configuration via an incision 20, as further described below, and that a substantial portion of the iris 16 in the vicinity of the incision 20 is covered by the iris engaging portion 12 of the iris protector 10 when inserted in the eye 14. In the non-limiting embodiment depicted in FIG. 1, the iris engaging portion 12 is a cuboid having a length l, a height h and a depth d, where l may be between 3.5 and 7 mm, h may be between 1.8 and 3 mm and d may be between 0.1 and 0.3 mm. In one non-limiting example, l=3 mm, h=2 mm and d=0.1 mm. In another non-limiting example, l=4 mm, h=1.8 mm and d=0.1 mm. The iris engaging portion 12 may have any other suitable shape (e.g., circular, oval, square and the likes) and/or dimensions in other embodiments.

In this embodiment, the iris engaging portion 12 generally comprises a central portion 22 and two lateral portions $24_1$, $24_2$ ending with respective lateral edges $26_1$, $26_2$. The iris engaging portion 12 is configured to be foldable along a single folding axis 27 generally located within the central portion 22 of the iris engaging portion 12 so as to generally minimize the overall size/dimensions of the iris protector 10 in its folded configuration to facilitate the insertion of the iris protector 10 in the eye 14. The iris engaging portion 12 is further configured to be foldable in one direction only so as to generally prevent the iris engaging portion 12 from pinching the iris 16 once inserted inside the eye 14.

The iris protector 10 further comprises folding handling members $28_1$, $28_2$ configured for facilitating a transition from the elongated configuration of the iris engaging portion 12 to its folded configuration. In use, the folding handling members $28_1$, $28_2$ conveniently enable a user to exert pressure onto the iris protector 10 and mechanically force the iris protector 10 into the folded configuration for insertion into, and removal from, the eye 14 via the incision 20. In this embodiment, the folding handling members $28_1$, $28_2$ are each attached to the iris engaging portion 12 via one respective end and each comprise an engagement element $30_1$, $30_2$ at a respective other end. In this embodiment, the engagement elements $30_1$, $30_2$ are configured to provide a mechanical engagement mean for an instrument manipulated by the user (e.g., tweezers, etc.) and may be a projection, a recess, a hook, a hole and the likes. In this embodiment, the folding handling members $28_1$, $28_2$ are two arcuate members generally positioned along each one of the lateral edges $26_1$, $26_2$ of the iris engaging portion 12 and projecting away from the iris engaging portion 12 such that (1) the folding handling members $28_1$, $28_2$ project outside of an anterior cavity of the eye 14 (i.e., a region between the iris 16 and the cornea 18) through the incision 20 when the iris engaging portion 12 of the iris protector 10 rests on the iris 16 in the elongated configuration; and (2) a smallest distance between the two folding members $26_1$, $26_2$ in the elongated configuration of the iris protector 10 generally corresponds to a width $W_i$ of the incision 20, with $W_i$ typically between 2.2 and 6 mm. The curvature of the folding handling members $28_1$, $28_2$ may be such that the folding handling members $28_1$, $28_2$ generally espouse a shape of a contour of the eye 14. In practical implementations, the folding handling members $28_1$, $28_2$ may be made of a bio-compatible, non-resilient material such that the shape of the folding handling members $28_1$, $28_2$ generally does not change when pressure is exerted on them. Alternatively, the folding handling members $28_1$, $28_2$ may also be integrally-formed with the iris engaging portion 12 such that they are made of the same material as the material of the iris engaging portion 12. The folding handling members $28_1$, $28_2$ may have any other suitable position relative to the iris engaging portion 12 in other embodiments.

The folding handling members $28_1$, $28_2$ may have any other suitable shape (e.g., generally straight, curved and the likes) and/or dimensions in other embodiments.

Figure 5:
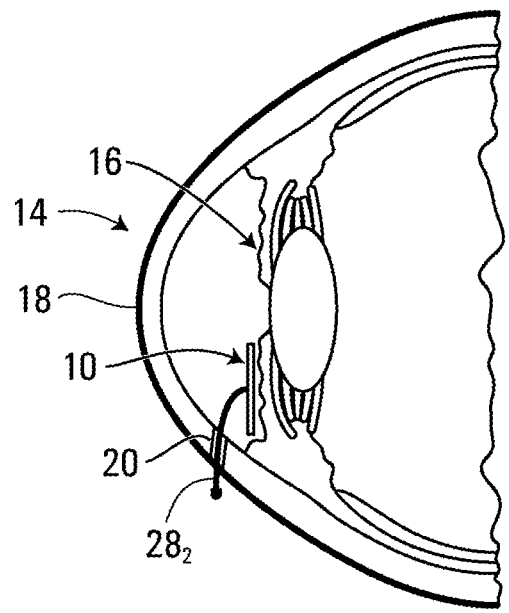
FIG. 5 shows a side-elevation cutaway view of the iris protector of FIG. 1 when inserted inside an eye.
Figure 6A:
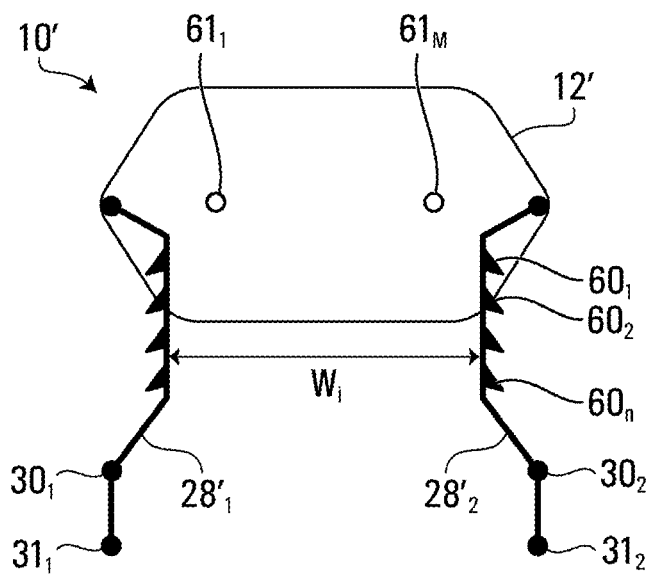
FIG. 6A shows an isometric view of a foldable iris protector having an oval iris engaging portion in an elongated configuration in accordance with a second specific embodiment.

FIG. 6A shows an iris protector 10' in accordance with a second specific embodiment. Similarly to the iris protector 10 shown in FIGS. 1 to 5, the iris protector 10' is foldable, that is the iris protector 10' can adopt an "elongated" configuration and a "folded" configuration.

Figure 7:
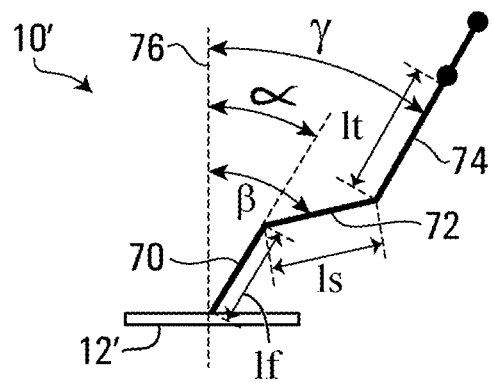
FIG. 7 shows a side-elevation view of the iris protector of FIG. 6A.
Figure 8:
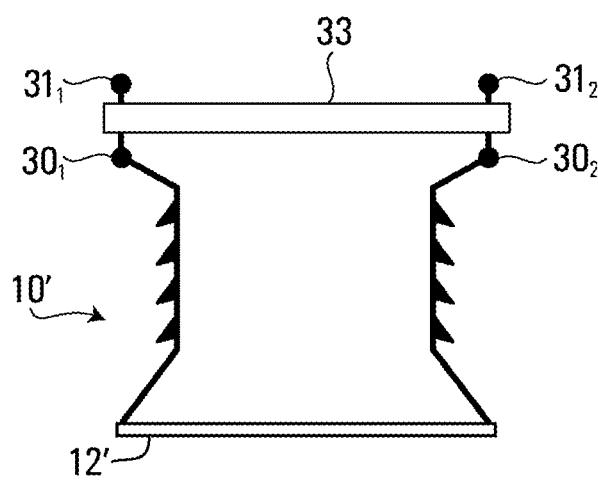
FIG. 8 shows a side-elevation view of the iris protector of FIG. 6A with the locking element of FIG. 6B.

According to this second embodiment and with further reference to FIGS. 7 and 8, the iris protector 10' comprises a substantially planar iris engaging portion 12' (which is analogous to iris engaging portion 12 shown in the first embodiment depicted in FIGS. 1 to 5) generally configured to rest directly on an iris once inserted inside an eye. The iris engaging portion 12' may be made of a resilient, shape-memory material such that the iris engaging portion 12' returns to the elongated configuration after being mechanically forced by a user into a folded configuration.

The iris protector 10' further comprises folding handling members $28'_1$, $28'_2$ (which are analogous to folding handling members $28_1$, $28_2$ shown in the first embodiment depicted in FIGS. 1 to 5) configured for facilitating a transition from the elongated configuration of the iris engaging portion 12' to its folded configuration.

In one non-limiting example, with reference to FIG. 7, when viewed from a lateral side of the iris engaging portion 12', each one of the folding handling members $28'_1$, $28'_2$ comprises a first section 70, a second section 72 and a third section 74. In specific embodiments, the first section 70 may have a length $l_f$ between 0.8 and 2 mm, the second section 72 may have a length $l_s$ between 1 and 3 mm and the third section 74 may have a length $l_t$ between 0.8 and 5 mm. The first section 70 is at an angle α with respect to a hypothetical line 76 perpendicular to a surface of the iris engaging portion 12' between 20° and 50°. The second section 72 is at an angle β with respect to the hypothetical line 76 perpendicular to the surface of the iris engaging portion 12' between 60° and 90°. The third section 74 is at an angle γ with respect to the hypothetical line 76 perpendicular to a surface of the iris engaging portion 12' between 0° and 150°. In the specific example of FIG. 7, $l_f$=1 mm, $l_s$=2 mm, $l_t$=3 mm, α=30°, β=75° and γ=30°. This configuration allows the folding members $28'_1$, $28'_2$ to extend outside of the anterior cavity of the eye through an incision when the iris engaging portion 12' of the iris protector 10' rests on the iris in the elongated configuration. This may also allow a user to manipulate the iris protector 10', including to insert the iris protector 10' inside an eye and remove the iris protector 10' from the eye, only via elements of the iris protector 10' that are located outside of the eye. The iris protector 10' may therefore be manipulated without inserting any instrument inside the eye 14, which may in turn reduce risks of damages to the incision and/or the cornea. Any other suitable configuration may be used in other embodiments (e.g., with various numbers of sections, various lengths of sections and angle between sections, etc.).

With reference to FIGS. 6A and 8, the folding handling members $28'_1$, $28'_2$ are shown as further exhibiting an optional scale pattern with a plurality of projections $60_1$-$60_n$ along at least a portion of a length of the folding handling members $28'_1$, $28'_2$. These projections $60_1$-$60_n$ are configured to facilitate a mechanical engagement of the folding members $28'_1$, $28'_2$ by a user to allow the user to exert pressure on the folding handling members $28'_1$, $28'_2$ and fold the iris protector 10'. The person of skill will understand that presence of the plurality of projections $60_1$-$60_n$ is optional and that the iris protector 10' may be provided without such projections, in certain embodiments.

In some embodiments, such as the one depicted in FIG. 6A, the iris engaging portion 12' may optionally also comprise a plurality of holes $61_1$-$61_m$ configured to facilitate manipulation of the iris protector 10' (e.g., positioning the iris protector 10' inside an eye) using an instrument (e.g. a manipulator device), as will be further discussed below. The plurality of holes $61_1$-$61_m$ may be positioned in any suitable location on the iris engaging portion 12'. In addition the number of holes may vary between implementations. For example, there may be one hole, two holes, three holes or any suitable number of holes. It is to be appreciated that positioning of the iris protector 10' inside an eye may also be performed by inserting an instrument (e.g. a manipulator as further described below, etc.) inside the eye through an incision.

Figure 6B:
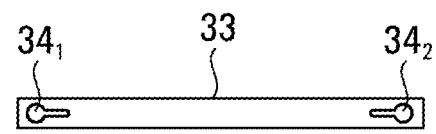
FIG. 6B shows a plan view of a locking element for use with the foldable iris protector of FIG. 6A.

In yet further embodiments, such as the one depicted in FIG. 6A, the iris protector 10' may further comprise optional locking means $31_1$, $31_2$ at respective ends of the folding handling members $28'_1$, $28'_2$. The locking means $31_1$, $31_2$ are configured for interlocking engagement with respective openings $34_1$, $34_2$ of a locking element 33 shown in FIG. 6B. The locking means $31_1$, $31_2$ and the locking element 33 may be made of a material including polypropylene, a flexible surgical-grade polymer, silicon, acrylic, nitinol, or any other suitable biocompatible material. In use, the interlocking engagement between the locking means $31_1$, $31_2$ and the locking element 33 contribute to the stabilization of the iris protector 10' when inserted in the eye 14. Any suitable configuration of the locking element and locking means $31_1$, $31_2$ (i.e., shape and size of the locking means $31_1$, $31_2$, corresponding shape and size of the respective openings $34_1$, $34_2$, position of the openings $34_1$, $34_2$ on the locking element 33, shape and size of the locking element 33, etc.) may be suitable in other embodiments.

Figure 10A:
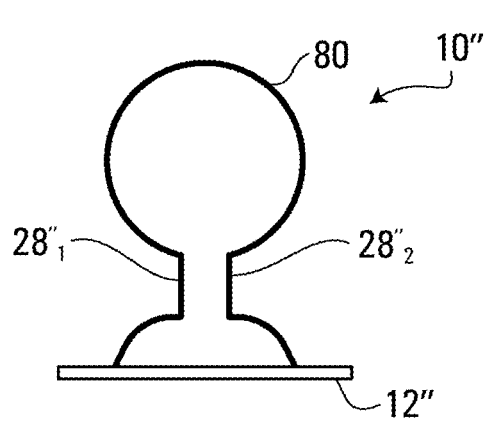
FIG. 10A shows a front elevation view of a foldable iris protector having an oval iris engaging portion in an elongated configuration in accordance with a third specific embodiment.

FIG. 10A shows an iris protector 10" in accordance with a third specific embodiment. Similarly to the iris protector 10 shown in FIGS. 1 to 5, the iris protector 10" is foldable, that is the iris protector 10" can adopt an "elongated" configuration and a "folded" configuration.

Figure 10B:
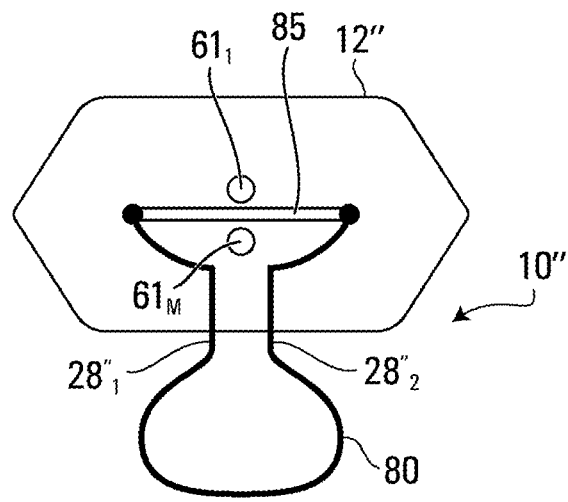
FIG. 10B shows an isometric view of the foldable iris protector of FIG. 10A.
Figure 10C:
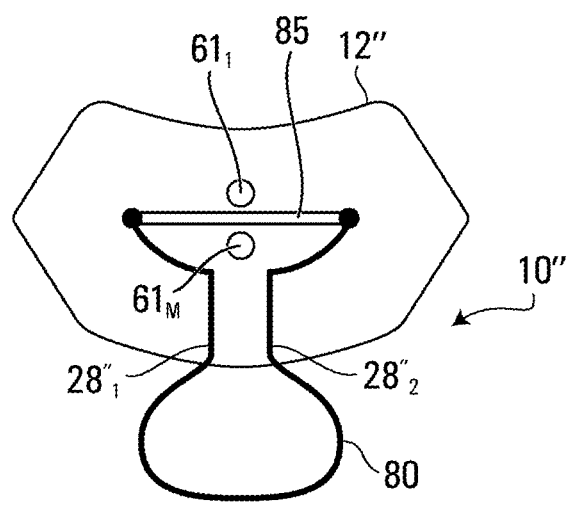
FIG. 10C shows an isometric view of a variant of the foldable iris protector of FIG. 10A.

According to this third embodiment and with further reference to FIGS. 10A, 10B and 10C the iris protector 10" comprises a substantially planar iris engaging portion 12" (which is analogous to iris engaging portion 12 shown in the first embodiment depicted in FIGS. 1 to 5) generally configured to rest directly on an iris once inserted inside an eye. The iris engaging portion 12" may be made of a resilient, shape-memory material such that the iris engaging portion 12" returns to the elongated configuration after being mechanically forced by a user into a folded configuration. The variant shown in FIG. 10C includes a modified profile for the engaging portion 12", which has a curved profile so as to better engage with the curved surface of an iris 16 when inserted in an eye.

The iris protector 10" further comprises folding handling members $28"_1$, $28"_2$ (which are analogous to folding handling members $28_1$, $28_2$ shown in the first embodiment depicted in FIGS. 1 to 5) configured for facilitating a transition from the elongated configuration of the iris engaging portion 12" to its folded configuration.

In one non-limiting example, with reference to FIGS. 10B and 10C, the planar iris engaging portion 12" may include a rod 85 linking the attachment points of folding handling members $28"_1$ and $28"_2$. The rod 85 may be made of a resilient, shape-memory material such that the rod 85 assists the iris engaging portion 12" to recover its elongated configuration. The rod 85 may be made of material including polypropylene, a flexible surgical-grade polymer, silicon, acrylic, nitinol (nickel titanium) or any other suitable biocompatible material.

Figure 11:
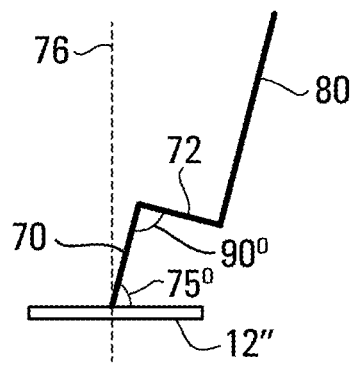
FIG. 11 shows a side elevation view of the foldable iris protector of FIG. 10A.

In one non-limiting example, with reference to FIG. 11, when viewed from a lateral side of the iris engaging portion 12", each one of the folding handling members $28'_1$, $28'_2$ comprises a first section 70, a second section 72 and a third section 80, where the third section forms a loop (as shown in FIGS. 10A and 10B). In specific embodiments, the first, second and third sections may have dimensions similar to those described with respect to the corresponding sections of the iris protector 10' described and shown with respect to FIG. 7. The first section 70 is at an angle α with respect to a hypothetical line 76 perpendicular to a surface of the iris engaging portion 12" between 15° and 50°. The second section 72 is at an angle β' with respect to the internal angle formed by the first section 70 and second section 72 between 60° and 100°. The third section 80 is at an angle γ with respect to the hypothetical line 76 perpendicular to a surface of the iris engaging portion 12" between 0° and 150°.

Turning back to FIGS. 4 and 5, an example of use of iris protector 10 will now be described. It is noted that, in use during an ophthalmic surgical procedure such as a cataract surgery, an incision 20 is first made in the anterior chamber of the eye 14, typically adjacent an outer edge of the iris 16 in a peripheral region of the cornea 18, the incision 20 being typically between 2 and 3.2 mm in length. Various preliminary steps may be performed in the surgical procedure prior to the introduction inside the eye 14 of the iris protector 10 but should at least include the introduction of a viscoelastic material inside the anterior chamber of the eye 14 to preserve or create space for safe introduction of the iris protector 10 inside the eye.

The iris protector 10 may then be folded by a user by exerting pressure on the folding handling members $28_1$, $28_2$ using an instrument (e.g. an applicator such as tweezers, etc.). The iris protector 10 in its folded configuration may then be inserted into the anterior chamber of the eye 14 via the incision 20 until (1) an entirety of the iris engaging portion 12 is inside the eye 14 and (2) the iris engaging portion 12 is generally positioned in a vicinity of the iris 16 and the incision 20 with the two folding members $28_1$, $28_2$ projecting outside of the anterior chamber of the eye 14 through the incision 20. The user may then release the pressure exerted onto the two folding handling members $28_1$, $28_2$ such that the iris protector 10 reverts to its elongated configuration inside the eye 14. In its elongated configuration inside the eye 14, at least a portion of the folding members $28_1$, $28_2$ including the engagement elements $30_1$, $30_2$ remain outside of the eye 14. The iris protector 10 may be inserted inside the eye 14 any time after the incision 20 is created. It is also appreciated that, in other non-limiting embodiments, the iris protector 10 may be inserted inside the eye 14 without being folded, i.e. directly in its unfolded configuration.

Figure 14A:
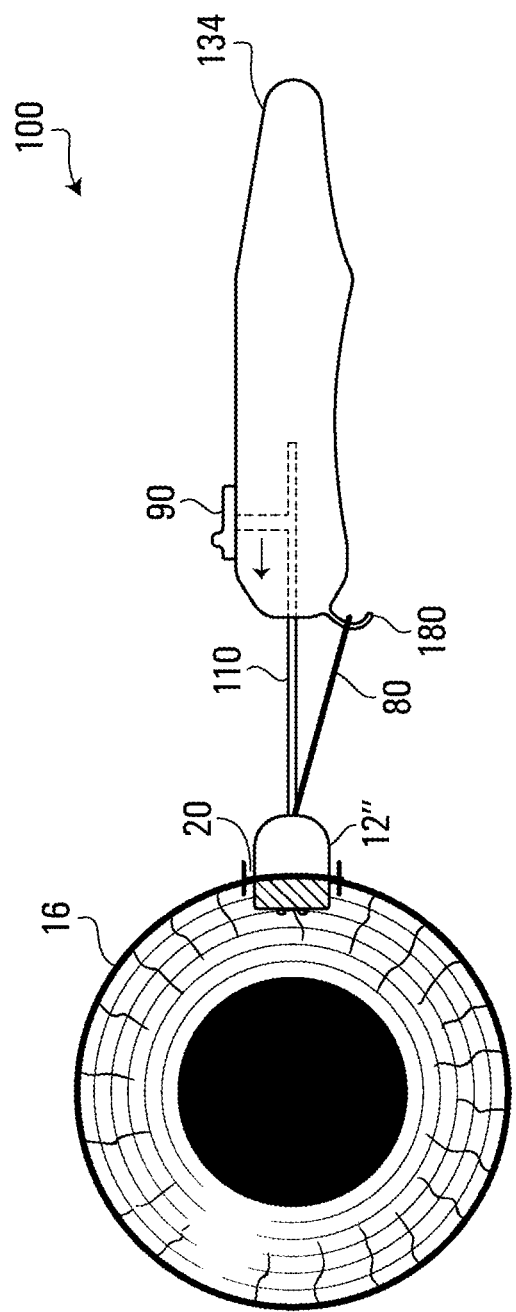
FIG. 14A to FIG. 14C show steps for inserting the iris protector of FIG. 10A inside an eye in accordance with a specific embodiment.
Figure 14B:
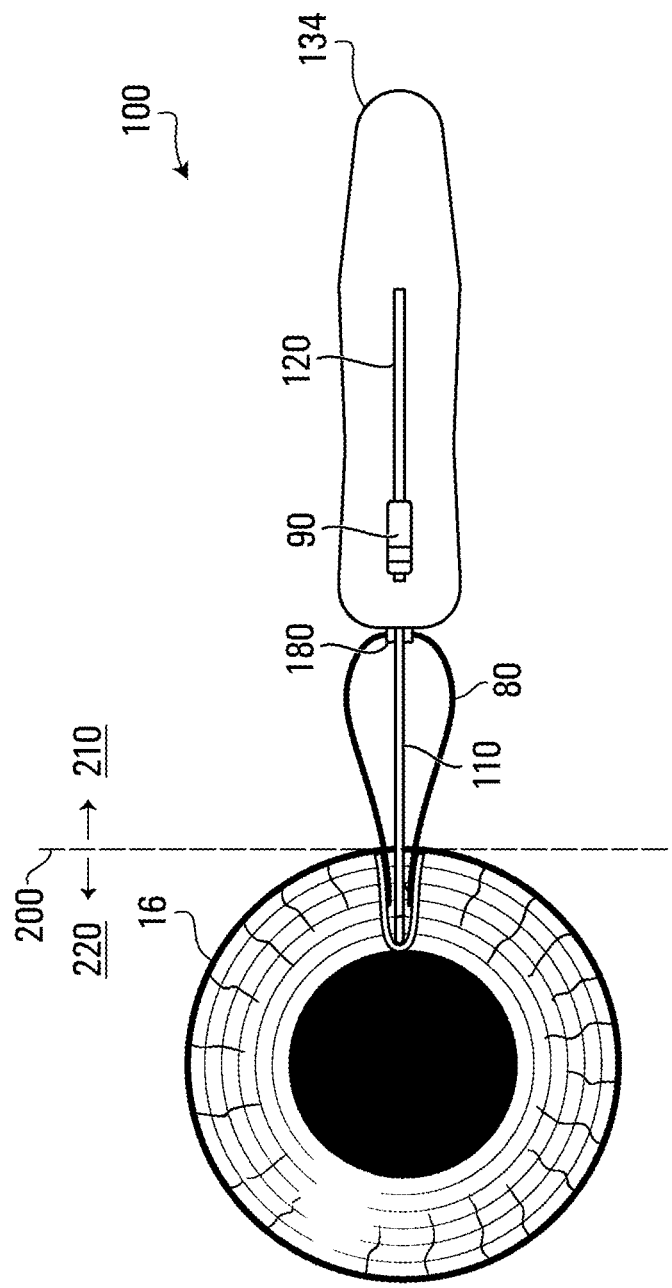

While the example depicted in FIGS. 4 and 5 shows the embodiment of the iris protector 10 shown and described with reference to FIGS. 1 to 3, the person skilled in the art will appreciate in view of the present description that the second embodiment of the iris protector 10' shown and described with reference to FIG. 6 to 8 or that the third embodiment of the iris protector 10" shown and described with reference to FIGS. 14A and 14B may be used and manipulated in a similar manner.

It is to be appreciated that, in the first, the second and third embodiments described, no further positioning of the iris protector 10 10' 10" may be necessary after insertion into the eye 14 and release of the iris protector 10 10' 10" to its elongated configuration since the positioning of the iris protector 10 10' 10" inside the eye 14 is dictated at least in part by the geometrical configuration of the folding handling members $28_1$, $28_2$ (or folding handling members $28'_1$, $28'_2$, or folding handling members $28"_1$, $28"_2$) and the mechanical pressure exerted by the edges of the incision 20 onto the two folding handling members $28_1$, $28_2$ (or folding handling members $28'_1$, $28'_2$, or folding handling members $28"_1$, $28"_2$). In other embodiments, positioning of the iris protector 10 10' 10" in its elongated configuration inside the eye 14 may be performed and/or adjusted by directly manipulating the portion of the two folding handling members $28_1$, $28_2$ (or folding handling members $28'_1$, $28'_2$, or folding handling members $28"_1$, $28"_2$) or of the loop 80 (in the case of the iris protector 10") outside of the eye 14 or by using an instrument (e.g. a manipulator as described later) where the iris engaging portion comprises the plurality of holes $61_1$-$61_m$. Where an instrument is used, as further described below, the instrument may be inserted inside the eye 14 through the incision 20.

With the iris protector 10 10' 10" in place, as a pressure inside a region anterior to the lens of the eye 14 increases during surgery, such as but not limited to when a dispersive visco-elastic material is introduced in the eye 14, or during hydrodissection and hydrodelineation of the crystalline lens, movement of the iris 16 toward the incision 20 in response to such increase in pressure is prevented by the iris protector 10 10' 10" which remains positioned between the iris 16 and the incision 20. Therefore, the iris protector 10 10' 10" mechanically prevents movement of the iris 16 towards the incision 20 and further prevents any portion of the iris 16 located in the vicinity of the incision 20 from prolapsing through the incision 20. In parallel, the iris protector 10 10' 10" may also maintain a shape of the incision 20 via the respective folding members $28_1$, $28_2$ or folding handling members $28'_1$, $28'_2$, or folding handling members $28''_1$, $28''_2$, such that a surgical instrument or any other material from outside of the eye 14 may be inserted inside the anterior cavity of the eye 14, or any other region of the eye 14, through the incision 20 while the iris protector 10 10' 10" remains in position inside the eye 14.

Optionally, in cases where more than one incision 20 is created in the eye 14 during a surgical procedure, one iris protector 10 10' 10" may be used for each one of the incisions to prevent movement of the iris 16 towards the incisions. Alternatively, a larger iris protector 10 10' 10" may be used to prevent movement of the iris 16 towards the incisions. The user may for example proceed with making an insertion which is of a dimension that corresponds to that one of the protector to ensure that the protector sits on the iris 16 while minimizing risk of having same inadvertently exit the incision.

With the iris protector 10 10' 10" in place inside the eye 14, the surgical procedure may then be pursued according to conventionally-accepted procedures. When the ophthalmic surgical procedure is completed or when iris prolapse is no longer a concern, the iris protector 10 10' 10" may be removed from the eye 14 via the incision 20. The iris protector 10 10' 10" is not left inside the eye 14 after the ophthalmic surgical procedure has been completed. It is appreciated that, in order to remove the iris protector 10 10', the user may fold the iris protector 10 10' by mechanically exerting pressure on the respective folding handling members $28_1$, $28_2$, or folding handling members $28'_1$, $28'_2$, using a suitable instrument (e.g., suitable tweezers, etc.). This is advantageous since it enables removal of the iris protector 10 10' from the eye 14 via manipulation of only portions of the iris protector 10 10' (i.e., the folding handling members $28_1$, $28_2$, or folding handling members $28'_1$, $28'_2$) outside of the eye 14 and that projects through the incision 20, thereby reducing risks of contact with and/or damage to the cornea 18. The manner in which the iris protector 10" is inserted and removed from the eye will be described later in this text.

After the iris protector 10 10' 10" has been removed from the eye 14, the ophthalmic surgical procedure may proceed and/or conclude according to conventionally-accepted procedures. It is to be noted that while the iris protector 10 10' 10" may be used during an ophthalmic surgical procedure such as a cataract surgery, the iris protector 10 10' 10" may also be introduced in the eye of at-risk patient (i.e., patient with iris prolapse in the other eye, obese patients with high blood pressure, patients with intraoperative floppy iris (IFIS) syndrome and the likes) as a prophylactic measure.

Figure 12A:
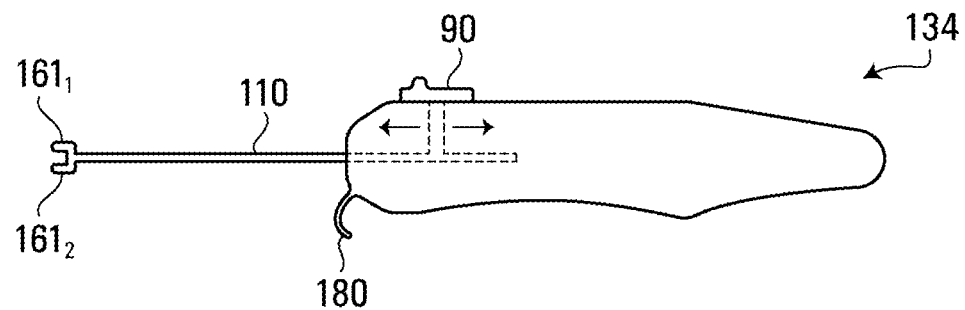
FIG. 12A shows a side elevation view of a manipulator for use with the iris protector of FIG. 10A in accordance with a specific embodiment.
Figure 12B:
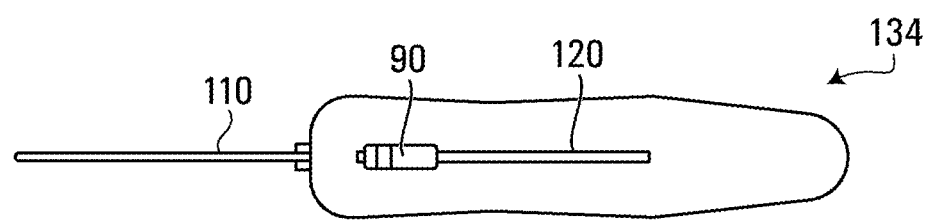
FIG. 12B shows a vertical elevation view of the manipulator of FIG. 12A.

FIGS. 12A and 12B show a manipulator 134 for use with the iris protector 10" shown and described with respect to FIGS. 10A and 10B. In this embodiment, the manipulator 134 encloses a sliding sleeve 120 configured for receiving an actuator 90 which is coupled to an injecting rod 110. The actuator 90 is configured for allowing a user to displace the injecting rod 110 along a longitudinal axis of the manipulator 134 such that the injecting rod 110 can slide from an extended position away from the manipulator 134 to a retracted position, where the injecting rod 110 can be partially enclosed within the body of the manipulator 134. Other suitable configurations can be envisaged for displacing the injecting rod 110 in other embodiments.

Figure 13A:
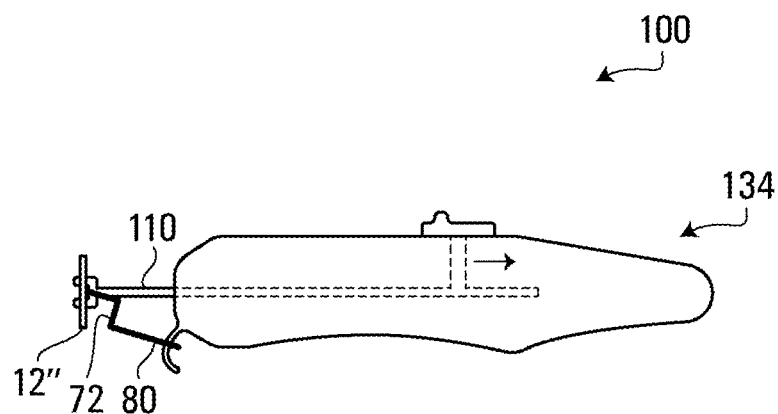
FIG. 13A shows a side elevation view of the manipulator of FIG. 12A together with the iris protector of FIG. 10A, where the iris protector is in an elongated configuration.

In this embodiment, the manipulator 134 includes a loop engaging element 180 configured for engaging at least a portion of the loop 80 of the iris protector 10" as shown in FIG. 13A. The loop engaging element 180 may have any suitable shape and dimension. However, it is appreciated that the shape and dimensions of the loop engaging portion 180 is preferably configured to ensure that when engaged, the loop 80 is secured to the manipulator 134 to prevent accidental dropping of the iris protector 10" during eye surgery. In this embodiment, the injecting rod 110 and the loop engaging element 180 cooperate to confer a folded or elongated configuration to the iris protector 10" as will further described with respect to FIGS. 13A and 13B.

Figure 13B:
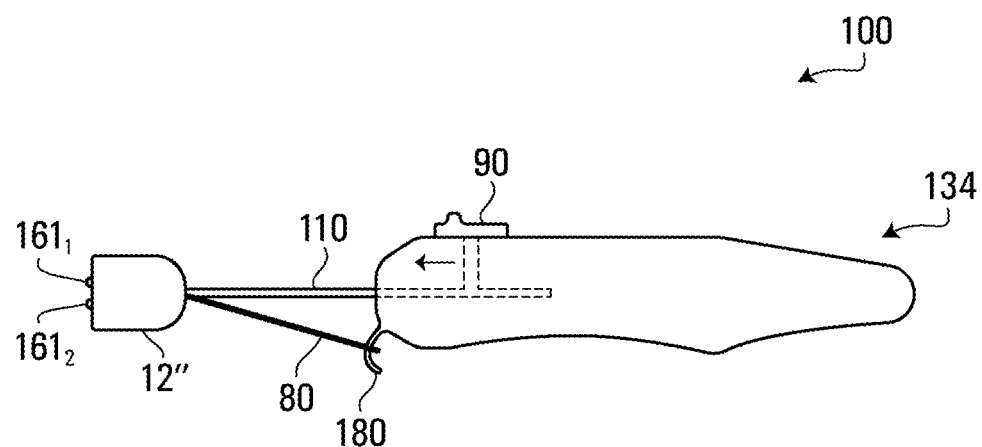
FIG. 13B shows a side elevation view of the manipulator and iris protector of FIG. 13A, where the iris protector is in a folded configuration.

FIG. 13A shows a system 100 that includes the manipulator 134 loaded with iris protector 10". The injecting rod 110 may have one or more engaging elements $161_1$, $161_2$ configured for engaging the one or more holes $61_1$, $61_M$, on the iris protector 10". The iris protector 10" may then be folded by a user by sliding the actuator 90 in a direction towards the iris engaging portion 12" which results in the one or more engaging elements $161_1$, $161_2$ pushing against the iris engaging portion 12 while the loop 80 is being retained by the loop engaging element 180, as shown in FIG. 13B. The iris protector 10" in its folded configuration may then be inserted into the anterior chamber of the eye 14 via the incision 20 until (1) an entirety of the iris engaging portion 12" is inside the eye 14 and (2) the iris engaging portion 12" is generally positioned in a vicinity of the iris 16 and the incision 20 with the two folding members $28''_1$, $28''_2$ projecting outside of the anterior chamber of the eye 14 through the incision 20, as shown in FIG. 14A. In order to ensure that once installed inside the eye 14, the iris engaging portion 12" is secured inside the intra-eye area 220 and does not slide through imaginary boundary 200 back to exterior area 210, the user may rotate the system 100 at a suitable angle, preferably of 90°, as shown in FIG. 14B such that the iris engaging portion 12" is at an angle relative to the incision 20 and cannot easily slip out therefrom.

Figure 14C:
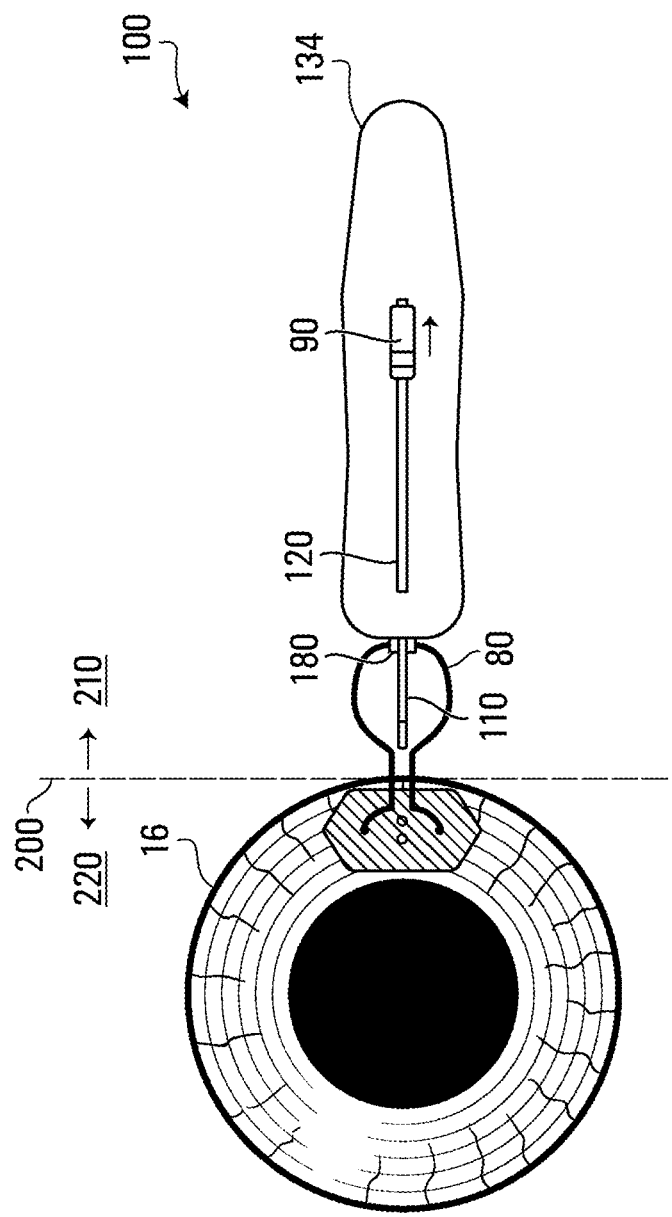
Figure 14D:
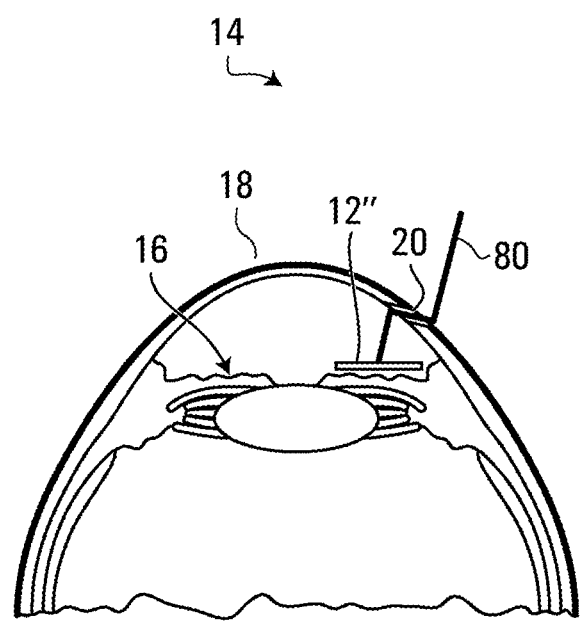
FIG. 14D shows the iris protector of FIG. 10A inside an eye.

The user may then slide the actuator 90 in a direction away from the iris engaging portion 12" such that the iris protector 10" reverts to its elongated configuration, inside the eye 14, as shown in FIG. 14C. In its elongated configuration inside the eye 14, at least a portion of the folding members $28_1''$, $28_2''$ including the loop 80 remain outside of the eye 14 as shown in FIG. 14D.

The iris protector 10" is not left inside the eye 14 after the ophthalmic surgical procedure has been completed. It is appreciated that, in order to remove the iris protector 10", the user may fold the iris protector 10" by using the manipulator 134 in the reverse order described with respect to FIGS. 14A to 14C. Alternatively, the use may simply pull on the iris protector 10" to remove same from the eye but without having it adopt the folded configuration.

Figure 9:
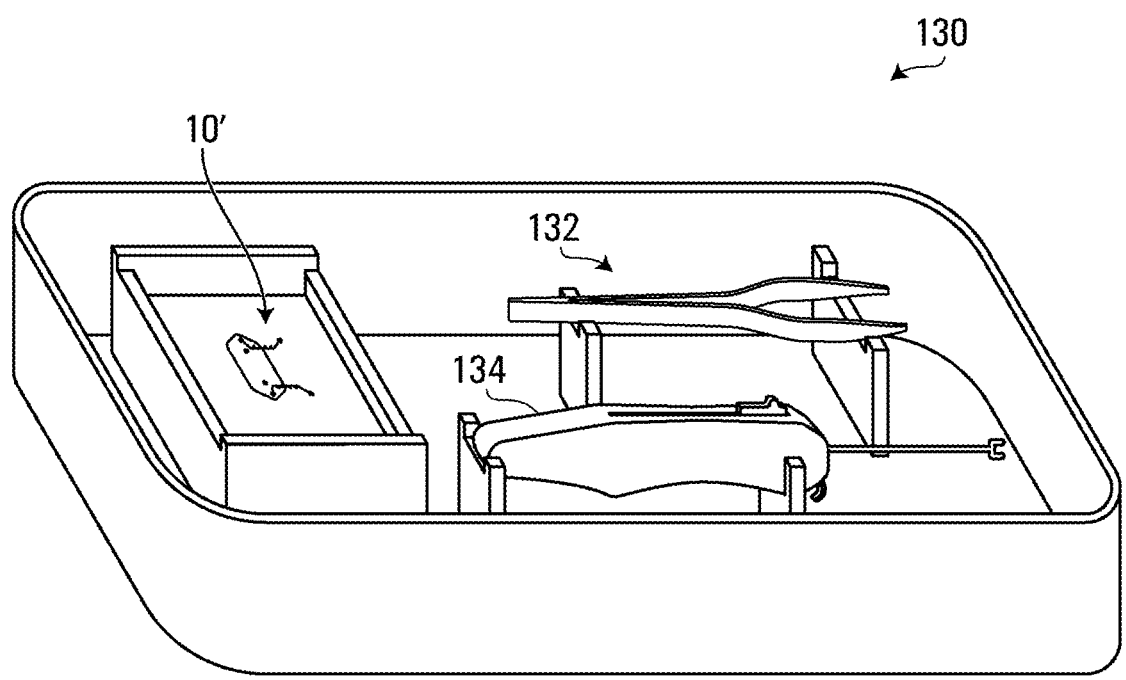
FIG. 9 shows an isometric view of a kit comprising the iris protector of FIG. 6A in accordance with a specific embodiment.

Returning to FIG. 9, the iris protector 10 10' 10" may be provided as part of a sterilized kit 130 alone or with an instrument such as an applicator 132 (e.g. tweezers, etc.), a scalpel (not shown), and/or the manipulator 134 or any combination thereof. Preferably, the iris protector 10 10' 10" is provided as part of a sterilized kit with a corresponding applicator 132, and/or a manipulator 134 whereby dimensions of the iris protector 10 10' 10" generally correspond to the dimensions of the corresponding applicator and/or the corresponding manipulator 134 to be used with the iris protector 10 10' 10" during an ophthalmic surgical procedure.

Certain additional elements that may be needed for operation of some embodiments have not been described or illustrated as they are assumed to be within the purview of those of ordinary skill in the art. Moreover, certain embodiments may be free of, may lack and/or may function without any element that is not specifically disclosed herein.

Any feature of any embodiment discussed herein may be combined with any feature of any other embodiment discussed herein in some examples of implementation.

In case of any discrepancy, inconsistency, or other difference between terms used herein and terms used in any document incorporated by reference herein, meanings of the terms used herein are to prevail and be used.

Although various embodiments and examples have been presented, this was for purposes of describing, but is not limiting. Various modifications and enhancements will become apparent to those of ordinary skill in the art.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the disclosure have been described and illustrated, it will be apparent to those skilled in the art in light of the present description that numerous modifications and variations can be made. The scope of the invention is defined more particularly in the appended claims.

The invention claimed is:

1. An iris protector for use in reducing occurrences of prolapse of iris tissue during ophthalmic surgical procedures, said iris protector comprising:
   a. a substantially planar iris engaging portion configured to rest directly on an iris once inserted inside an eye; and
   b. folding handling members extending from the substantially planar iris engaging portions wherein the folding handling members are secured to lateral portions of the iris engaging portion at respective first ends of the folding handling member and the folding handling members comprise engagement elements positioned at respective second ends of the folding handling members.

2. The iris protector of claim 1, wherein the iris engaging portion is made of a bio-compatible material.

3. The iris protector of claim 1, wherein the iris engaging portion is made of a resilient material.

4. The iris protector of claim 3, wherein the resilient material includes polypropylene, silicon, nitinol, acrylic or any combination thereof.

5. The iris protector of claim 1, wherein the iris engaging portion is foldable.

6. The iris protector of claim 5, wherein the iris engaging portion is foldable along a folding axis located in a central portion of the iris engaging portion.

7. The iris protector of claim 5, wherein the iris engaging portion is foldable in one direction only.

8. The iris protector of claim 1, wherein said substantially planar iris engaging portion is configured for:
   a. acquiring a folded configuration in response to application of a force to the folding handling members; and
   b. reverting to an elongated configuration after the force to the folding handling members ceases to be applied.

9. The iris protector of claim 1, wherein the iris engaging portion comprises one or more holes configured for facilitating manipulation of the iris protector.

10. The iris protector of claim 1, wherein the engagement elements includes a projection.

11. The iris protector of claim 1, wherein the engagement elements includes a recess.

12. The iris protector of claim 1, wherein the engagement elements includes a hook.

13. An iris protector for use in reducing occurrences of prolapse of iris tissue during ophthalmic surgical procedures, said iris protector comprising:
   a. a substantially planar iris engaging portion configured to rest directly on an iris once inserted inside an eye; and
   b. folding handling members extending from the substantially planar iris engaging portion, wherein the folding handling members include a scale pattern extending along at least a portion of the folding handling members, the scale pattern including a plurality of projections configured to facilitate a mechanical engagement of the folding handling members with an instrument.

14. A sterilized kit for use during an ophthalmic surgical procedure, said sterilized kit comprising:
   an iris protector for use in reducing occurrences of prolapse of iris tissue during ophthalmic surgical procedures, said iris protector comprising:
      a. a substantially planar iris engaging portion configured to rest directly on an iris once inserted inside an eye, and
      b. folding handling members extending from the substantially planar iris engaging portion, wherein said folding handling members form together a loop, and
   a manipulator configured for mechanically engaging the loop.

15. The sterilized kit of claim 14, wherein said substantially planar iris engaging portion is configured for:
   a) acquiring a folded configuration in response to application of a first force to the loop in a direction substantially perpendicular to the substantially planar iris engaging portion while applying a second force to the substantially planar iris engaging portion in a direction parallel to the first force;
b) reverting to an elongated configuration after the first force to the loop ceases to be applied.

16. The sterilized kit of claim 14, wherein the manipulator is further configured for mechanically engaging the substantially planar iris engaging portion of the iris protector.

* * * * *